(12) United States Patent
Reyes

(10) Patent No.: US 9,044,293 B2
(45) Date of Patent: Jun. 2, 2015

(54) ORAL CAVITY SUCTION DEVICE

(71) Applicant: Hari Mark Reyes, Portland, OR (US)

(72) Inventor: Hari Mark Reyes, Portland, OR (US)

(*) Notice: Subject to any disclaimer, the term of this patent is extended or adjusted under 35 U.S.C. 154(b) by 0 days.

(21) Appl. No.: 13/901,796

(22) Filed: May 24, 2013

(65) Prior Publication Data

US 2014/0349249 A1 Nov. 27, 2014

(51) Int. Cl.
*A61C 17/06* (2006.01)

(52) U.S. Cl.
CPC .................... *A61C 17/043* (2013.01)

(58) Field of Classification Search
CPC .................... A61C 17/043; A61C 17/0208
USPC .............. 433/91–96; 600/237, 242, 239, 156, 600/387
See application file for complete search history.

(56) References Cited

U.S. PATENT DOCUMENTS

| | | | |
|---|---|---|---|
| 5,078,603 A * | 1/1992 | Cohen | 433/91 |
| 5,520,651 A * | 5/1996 | Sutcu et al. | 604/118 |
| 2008/0318183 A1* | 12/2008 | Suzman | 433/93 |
| 2009/0123886 A1* | 5/2009 | Vaska | 433/27 |

* cited by examiner

*Primary Examiner* — Yogesh Patel
(74) *Attorney, Agent, or Firm* — Mark S Hubert

(57) ABSTRACT

A disposable saliva ejector for connection with a slow-speed suction device has a suction end and a discharge end. The tapered ejector has an ovate shape. A retention orifice helps secure the ejector within the patient's mount, while a larger extraction orifice removes fluid and debris. Placement of the saliva ejector within the mouth lies along the interior of the patient's cheek, keeping the oral cavity clear of viewing obstructions. The discharge end connects to a discharge tube, wrapping around the oral commissure then hooking onto the patient's outer cheek. Once properly placed within the patient's mouth the dental assistant is relieved from providing suction during various procedures.

3 Claims, 6 Drawing Sheets

ORAL CAVITY SUCTION DEVICE

BACKGROUND OF THE INVENTION

Saliva ejectors are narrow tubes that dental health professionals employ for removing saliva, water, and debris during a dental procedure. Often saliva ejectors will "sit" in a patient's mouth during a dental procedure in order to continuously rid the mouth of excess saliva, water, and debris to facilitate uninterrupted work by the dental health professional. The ejector tubes are typically made of a pliable plastic with a metal wire embedded within its wall to allow the tube to be bent to a desired angle and maintain that angle. If the tip of the suction tube contacts the patient's mouth tissue, it can suck the tissue into contact with the tip of the ejector, thereby rendering the ejector useless, since it is no longer removing excess saliva, water, and debris, not to mention causing a very uncomfortable sensation for the patient. Due to this fact the dentist preforming the work on the patient must be assisted at all times.

SUMMARY OF THE INVENTION

The saliva ejector of the present invention solves the aforementioned problems. Employing a tapered, ovate shape. The saliva ejector of the present invention resides along the left or right-side buccal mucosa allowing for full view of the oral cavity. Placement along the buccal mucosa also alleviates the patient's natural gag reflex, and having different sized suction orifices on two opposing faces ensures a strong suction field while providing a gentle suction force on the patient's buccal mucosa and inner cheek helping to secure the position of the saliva ejector within the patient's mouth, resulting in a more effective, yet gentler saliva ejector. The patient can easily adjust his bite without the removal of the ejector, as well as relieve the water/saliva from his mouth by simply closing his mouth, thereby allowing the dentist or hygienist to work without an assistant constantly providing suction. The saliva ejector of the present invention also maximizes the patient's comfort if he has lingual gum sensitivity, temporomandibular joint (TMJ) issues, or mandibular or maxillary tori; these regions are simply not contacted due to the ejector's unique geometry, and its placement within the mouth.

DETAILED DESCRIPTION

Figure 12:
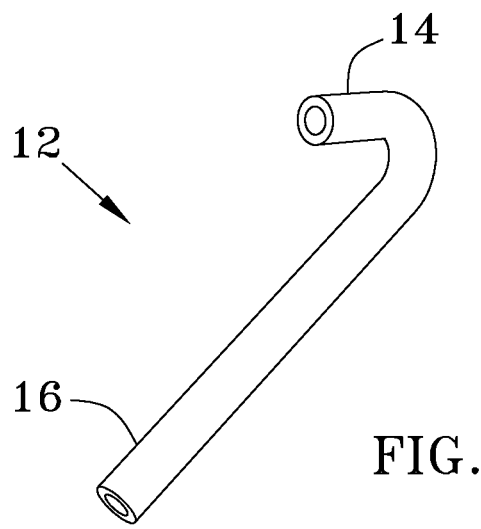
FIG. 12 is a perspective view of the discharge tube of the present invention.
Figure 13:
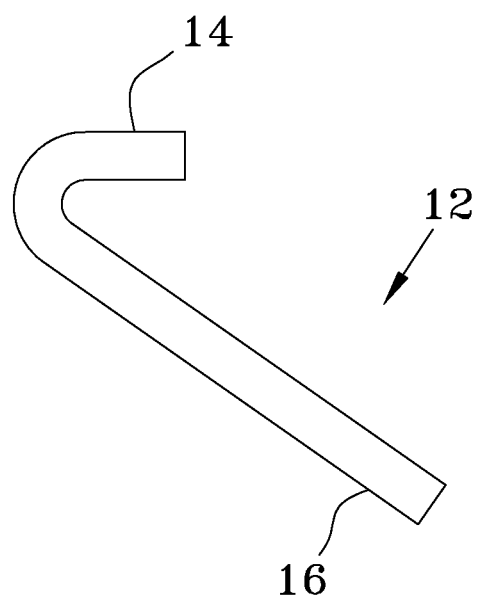
FIG. 13 is a left-side view of the discharge tube of the present invention.

Referring to FIG. 1-7, saliva ejector 10 of the present invention is shown. Discharge tube 12 is made of any suitable food grade or medical polymer for medical devices or stainless steel. Tube 12 is hollow, has a proximate end 14, a distal end 16, and is generally cane-shaped, in that the included angle at proximate end 14 is acute, forming an approximate 32° angle (see FIGS. 12-13). Discharge tube 12 can be reusable or disposable. It is through discharge tube 12 that saliva ejector 10 is connected to a slow-speed suction device (well known in the art and not shown), and through which saliva, water, and other debris are removed from the mouth of a patient.

Figure 7:
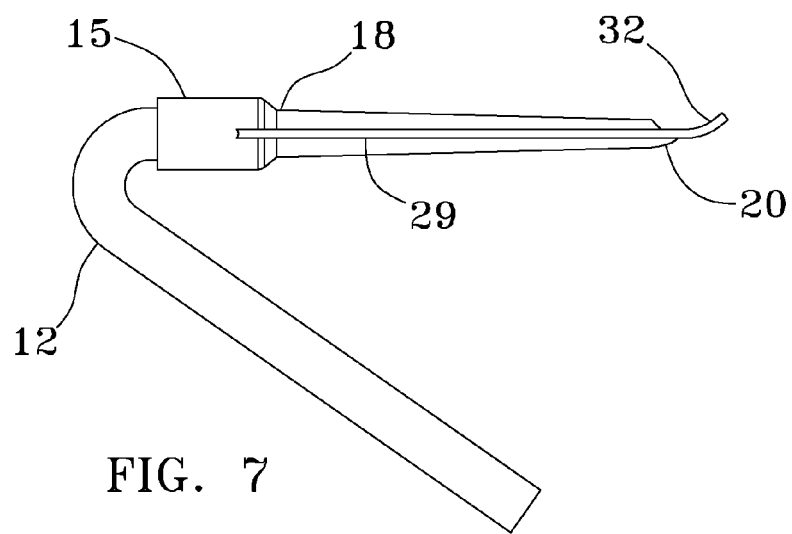
FIG. 7 is a left-side view of the saliva ejector of the present invention with the discharge tube attached.

Discharge tube 12 is removeably engaged via friction fit connection sleeve 15 located at the high-end 18 of saliva ejector 10. Turning to FIG. 7 it can be seen that there is a gradual uniform taper along saliva ejection tube 22 between high-end/back end 18 and a low-end/front end 20. Saliva ejection tube 22 extends along the longitudinal axis of saliva ejector 10, is hollow, and four-faced, channeling fluid and debris towards discharge tube 12. Best illustrated in FIGS. 8-11 it can be seen that saliva ejection tube 22, has a top face 24, a bottom face 26 (FIG. 8), and two rounded side faces 28. The top face 24 and bottom face 26 are planar and held in a spatial configuration, via side faces 28, that narrows in taper from high-end 18 to low-end 20.

Figure 1:
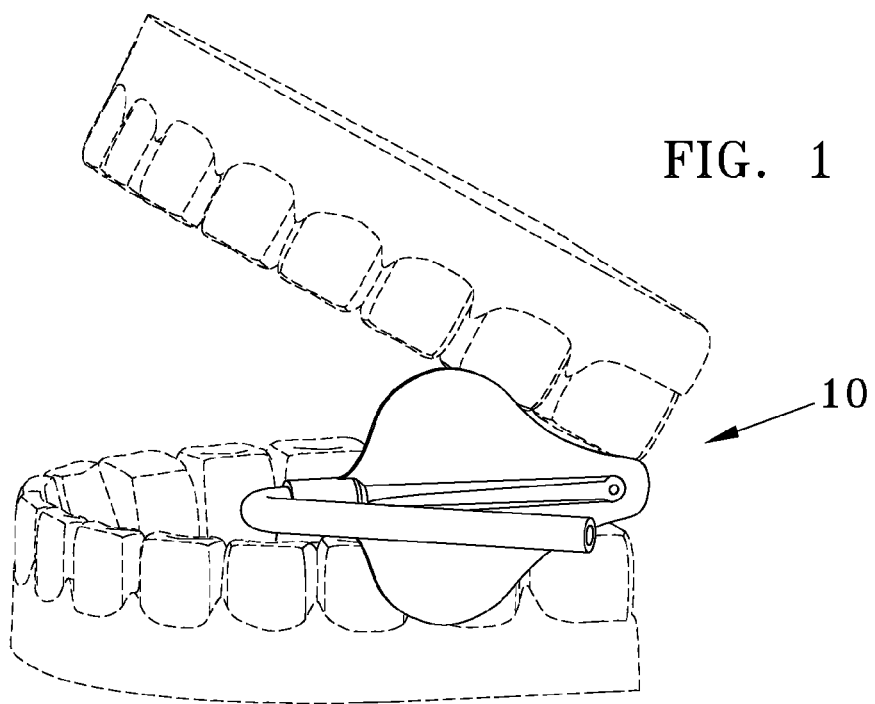
FIG. 1 is a cheek-side view of a dental model illustrating the saliva ejector of the present invention in an in-use position.
Figure 2:
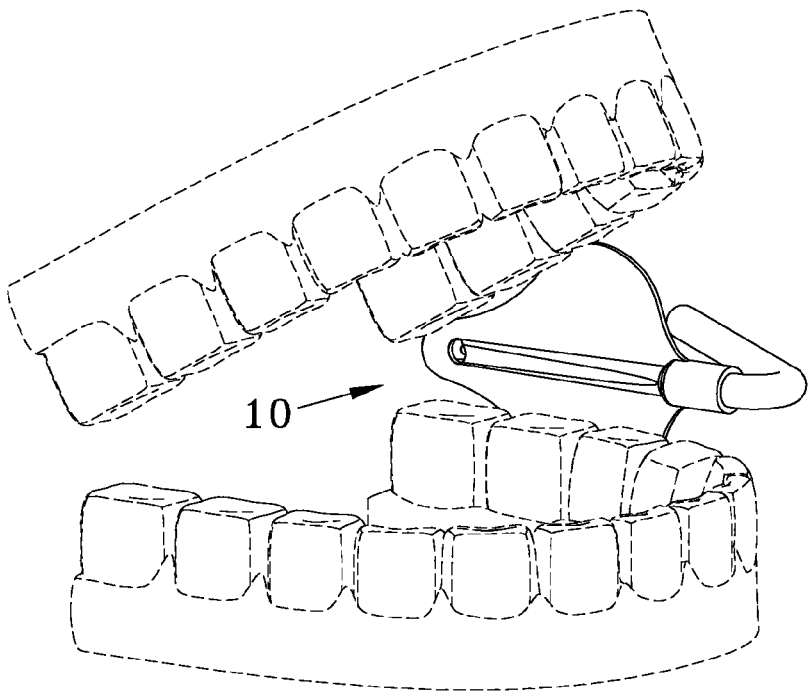
FIG. 2 is a tongue-side view of a dental model illustrating the saliva ejector present invention in an in-use position.
Figure 3:
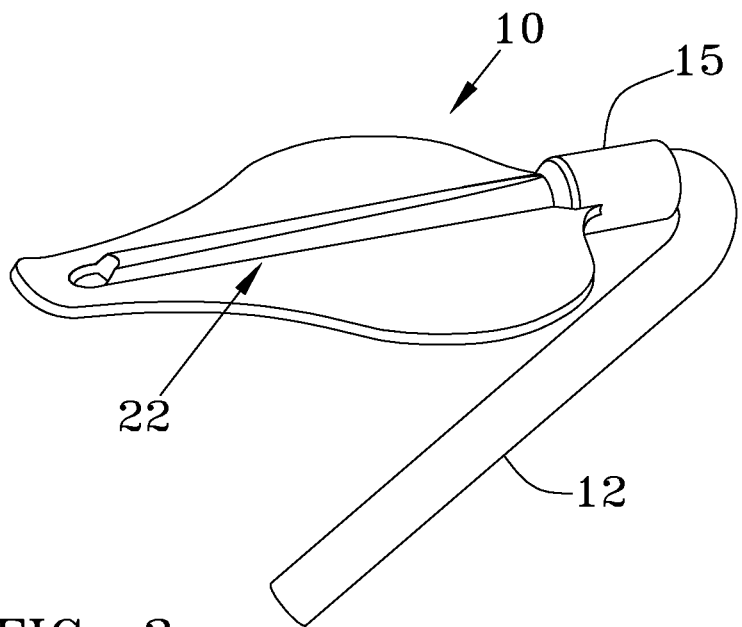
FIG. 3 is a perspective view of the saliva ejector of the present invention with the discharge tube attached.
Figure 4:
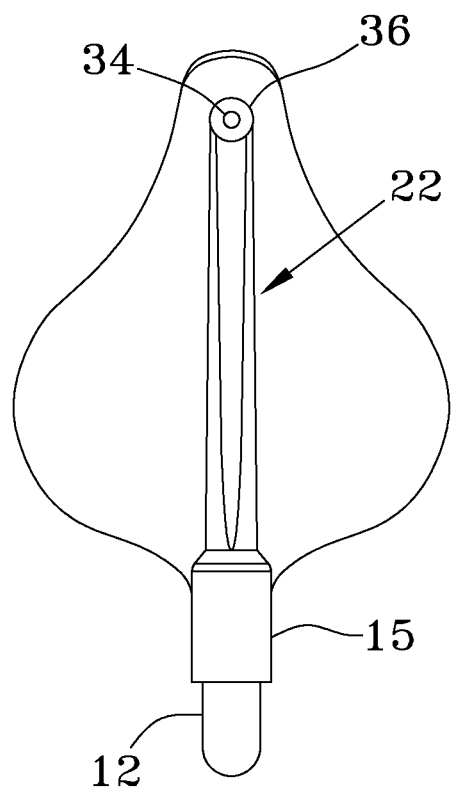
FIG. 4 is a top view of the saliva ejector of the present invention with the discharge tube attached.
Figure 5:
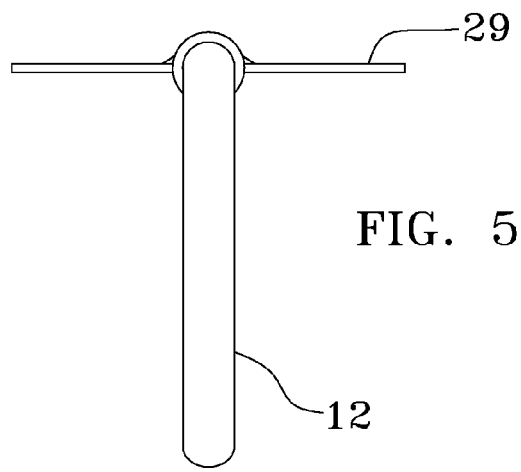
FIG. 5 is a back view of the saliva ejector of the present invention with the discharge tube attached.
Figure 6:
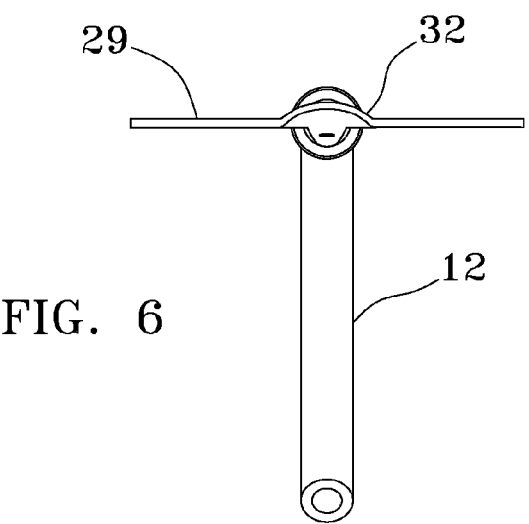
FIG. 6 is a front view of the saliva ejector of the present invention with the discharge tube attached.
Figure 8:
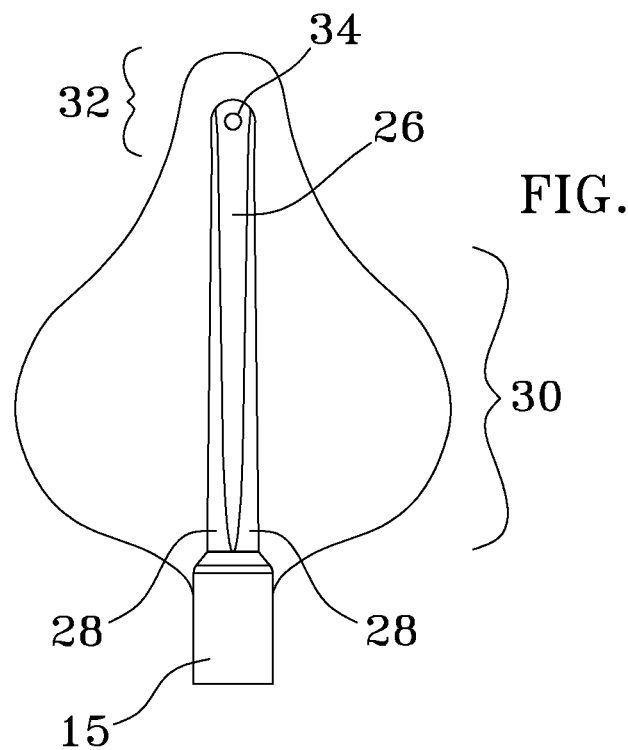
FIG. 8 is a bottom view of the saliva ejector of the present invention.
Figure 9:
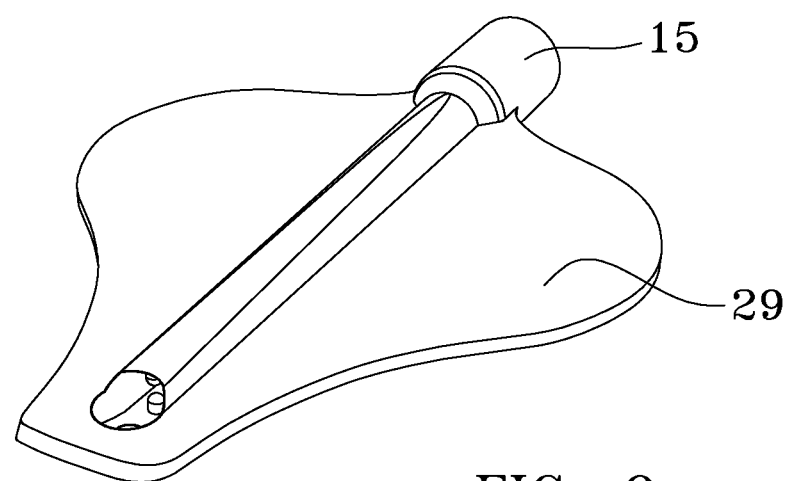
FIG. 9 is a front perspective view of the saliva ejector of the present invention.
Figure 10:
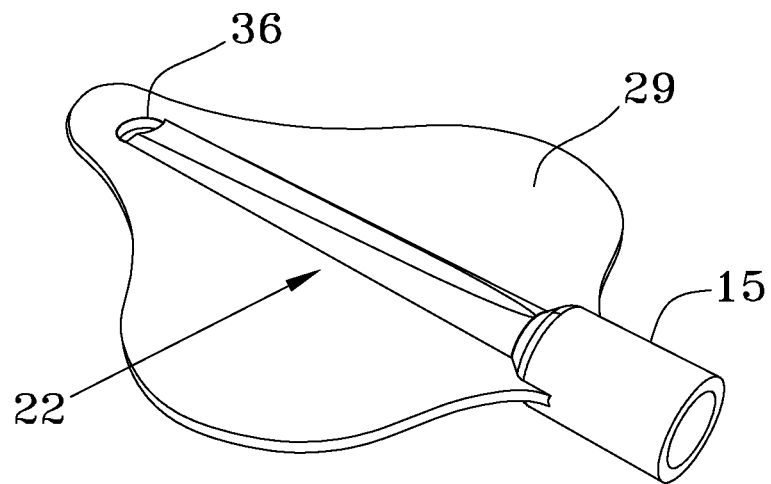
FIG. 10 is a back perspective view of the saliva ejector of the present invention.
Figure 11:
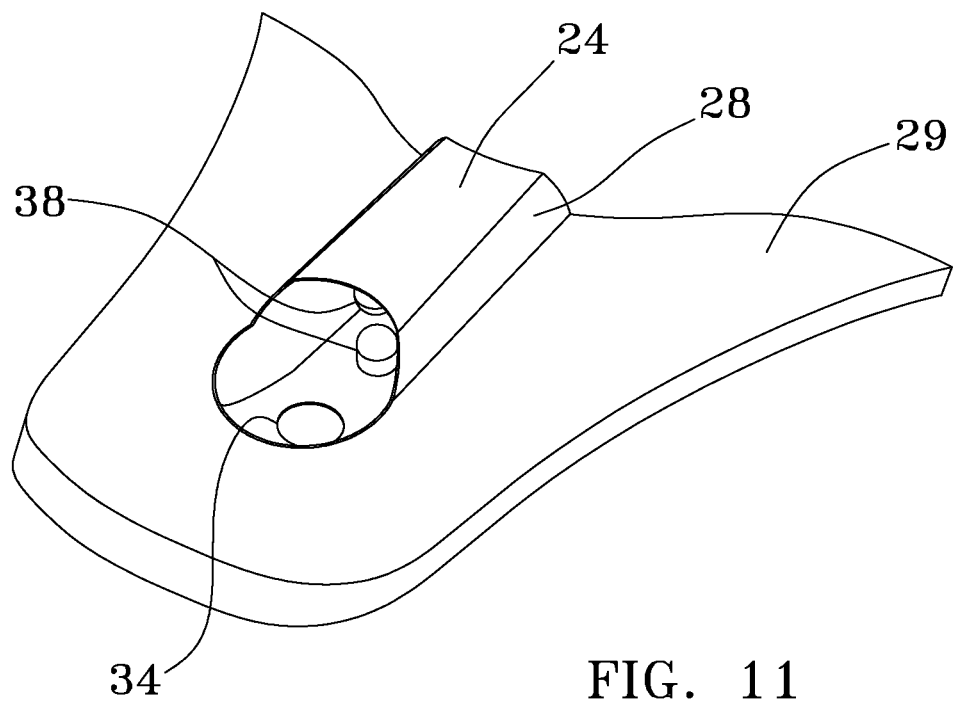
FIG. 11 is an enlarged partial view of the suction end of the saliva ejector of the present invention.

Placement leaf 29 provides the unique geometry of saliva ejector 10, which can generally be described as ovate (i.e., having a wider base than apex), such that placement leaf 29 has two distinct regions: 1) its body 30, and 2) its front lobe 32 (FIG. 8). Placement leaf 29 is a flexible, planar flange that is constructed from a medical grade flexible polymer of uniform thickness. Placement leaf 29 extends normally from the side faces 28 of the saliva ejector tube 22 extending around side faces 28 and extending beyond low-end 20 to form front lobe 32. The distribution of placement leaf 29 around saliva ejector tube 22 is uniform such that the longitudinal axis of saliva ejector 10 and the longitudinal axis of saliva ejection tube 22 are identical. Turning to FIGS. 6 and 7 it can be seen that front lobe 32 bends in an upward direction. When placed in the patient's mouth, front lobe 32 bends towards the lower region of the patient's retromolar area where saliva and water pools. Body 30 is designed to lie between the buccal regions of the oral cavity and the inner cheek, so as to not rely on teeth for support. No matter how the teeth are aligned or shaped, or even if the patient has missing teeth, the saliva ejector 10 will be fully supported and still function properly.

Retention orifice 34 is formed through bottom face 26 at, or adjacent to, the low-end 20 of saliva ejection tube 22, as is illustrated in FIG. 8. When saliva ejector 10 is connected to a low-speed suction device and placed properly along the buccal mucosa within the patient's mouth, bottom face 26 of saliva ejection tube will be secured to the patient's mouth via retention orifice 34. This design maximizes the surface area of saliva ejection tube 22 that contacts the retromolar region and/or the inner cheek, stabilizing saliva ejector 10 within the patient's mouth. The small diameter of retention orifice 34 limits the force/discomfort the patient feels from the suction and provides a quieter suction sound. An angled extraction orifice 36 is formed through top face 24 and side faces 28 at the low-end 20 of saliva ejection tube 22 and best illustrated in FIG. 11. The perimeter of extraction orifice 36 is larger than the perimeter of retention orifice 34. Still looking at FIG. 11 it can be seen that two anti-collapsing bosses 38 reside on and extend from the interior of saliva ejection tube 22, with one boss 38 extending from the interior surface of bottom face 26, and the other boss 38 extending from the interior surface of top face 24. Anti-collapsing bosses 38 are designed to touch one another under suction, preventing the interior cavity of saliva ejection tube 22 from completely collapsing under suction, and allowing the passage of water, salvia, and debris from extraction orifice 36 through saliva ejection tube 22, and out through discharge tube 12 via friction fit connection sleeve 15. Friction fit connection sleeve 15 is cylindrical in shape with a first open end located at high-end 18 of saliva ejection tube 22 and second open end sized for frictional engagement with the proximate end 14 of discharge tube 12.

In use, saliva ejector 10 is placed along the left-side or right-side of the buccal mucosa, such that bottom face 26 of ejection tube 22 resides along the inner cheek, and top face 24 of ejection tube 22 resides along the buccal side of the teeth. The discharge tube 12 curves around the oral commissure and then along the outside of the cheek. The placement of saliva ejector 10 is key to its function, since saliva pools in the lower regions of the oral cavity toward the throat. When properly placed within a patient's mount, saliva ejector 10 effectively removes the pooled saliva while not impeding the dentist's work. Once placed, saliva ejector 10 is comfortable for the patient and does not need constant monitoring from a dental assistant. Discharge tube 12 is connected to a low-speed suction device and once the low-speed suction device is turned on a diffuse yet effective suction field is created.

I claim:

1. A saliva ejector comprising:
a four-faced, tapered saliva ejection tube;
two anti-collapsing bosses;
a friction fit connection sleeve;
a placement leaf, said leaf having a uniform thickness;
an angled extraction orifice; and
a retention orifice;
wherein said saliva ejection tube is a linear, hollow member with a high-end and a low-end having a top face, a bottom face, and two curved side faces, wherein said top face and said bottom face are planar and held in a spatial configuration that narrows in taper from said high-end to said low-end by said side curved side faces;
wherein said extraction orifice is formed therethrough said top face of said low-end of said ejection tube;
wherein said anti-collapsing bosses are affixed to an interior surface and adjacent to said front end of said ejection tube;
wherein said retention orifice is formed therethrough said bottom face of said low-end of said saliva ejection tube between said anti-collapsing bosses and said low-end of said ejection tube;
wherein said friction fit connection sleeve has a first open end and a second open end, said first open end sized for frictionally engagement with a vacuum line of a slow-speed suction device, and said second open end affixed to said high-end of said saliva ejection tube;
wherein said placement leaf is a flexible, ovate-shaped, flange with a planar body and an upward-curved front lobe; wherein said planar body extends around said ejection tube such that a longitudinal axis of said placement leaf is spatially common with a longitudinal axis of said saliva ejection tube, and wherein said extraction orifice and said retention orifice reside within the front lobe portion of said placement leaf.

2. The saliva ejector of claim 1 wherein the perimeter of said retention orifice is smaller than the perimeter of said extraction orifice.

3. The saliva ejector of claim 1 further comprising a discharge tube, wherein said discharge tube has a distal and proximate end said distal end connectable to a low-speed suction device and said proximate end rigidly formed into a bend so that the included angle on said discharge tube is acute and wherein said discharge tube is removeably connected to said saliva ejection tube through said friction fit connection sleeve.

* * * * *